United States Patent
Kietzmann et al.

(10) Patent No.: US 11,547,803 B2
(45) Date of Patent: Jan. 10, 2023

(54) PEN-TYPE DRUG INJECTION DEVICE WITH CONTROLLER AND TIME LOCK-OUT MECHANISM FOR ITS DRIVE

(71) Applicant: Sanofi-Aventis Deutschland GmbH, Frankfurt am Main (DE)

(72) Inventors: Hardy Kietzmann, Frankfurt am Main (DE); Jasmin Groeschke, Frankfurt am Main (DE); Hanno Juhnke, Frankfurt am Main (DE); Jan-Peter Spengler, Frankfurt am Main (DE); Matthias Scharf, Frankfurt am Main (DE); Christoph Dette, Frankfurt am Main (DE); Michael Schrack, Pliezhausen (DE); Olaf Zeckai, Weinheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 824 days.

(21) Appl. No.: 16/031,962

(22) Filed: Jul. 10, 2018

(65) Prior Publication Data
US 2018/0318508 A1    Nov. 8, 2018

Related U.S. Application Data

(63) Continuation of application No. 14/359,383, filed as application No. PCT/EP2012/072945 on Nov. 19, 2012, now Pat. No. 10,058,655.

(30) Foreign Application Priority Data

Nov. 22, 2011 (EP) .................................. 11190062

(51) Int. Cl.
*A61M 5/315* (2006.01)
*G16H 40/63* (2018.01)
(Continued)

(52) U.S. Cl.
CPC .......... *A61M 5/31501* (2013.01); *A61M 5/24* (2013.01); *G16H 20/17* (2018.01);
(Continued)

(58) Field of Classification Search
CPC .............. A61M 5/24; A61M 2205/582; A61M 2205/581; A61M 2205/52;
(Continued)

(56) References Cited

U.S. PATENT DOCUMENTS 533,575 A    2/1895  Wilkens
4,417,889 A  11/1983 Choi
(Continued)

FOREIGN PATENT DOCUMENTS

CN    101495080 A    7/2009
CN    102083489 A    6/2011
(Continued)

OTHER PUBLICATIONS

International Search Report and Written Opinion for Application No. PCT/EP2012/072945, dated Dec. 19, 2012, 13 pages.

*Primary Examiner* — Lauren P Farrar
(74) *Attorney, Agent, or Firm* — McCarter & English, LLP

(57) ABSTRACT

The present invention relates to a drive mechanism for a drug delivery device, comprising: a piston rod to operably engage with a piston of a cartridge to displace the piston in a distal direction during a dose dispensing action, at least one actuation member mechanically coupled with the piston rod to induce a distally directed displacement of the piston rod when actuated by a user, a control to ascertain at least one predefined condition of use, and at least one interlock member coupled with the control to mechanically obstruct displacement of the piston rod if the condition of use is not fulfilled.

19 Claims, 4 Drawing Sheets

(51) Int. Cl.
  *G16Z 99/00* (2019.01)
  *A61M 5/24* (2006.01)
  *G16H 20/17* (2018.01)
  *A61M 5/20* (2006.01)

(52) U.S. Cl.
  CPC ............ *G16H 40/63* (2018.01); *G16Z 99/00* (2019.02); *A61M 5/31541* (2013.01); *A61M 2005/208* (2013.01); *A61M 2205/13* (2013.01); *A61M 2205/18* (2013.01); *A61M 2205/27* (2013.01); *A61M 2205/276* (2013.01); *A61M 2205/3324* (2013.01); *A61M 2205/3331* (2013.01); *A61M 2205/3569* (2013.01); *A61M 2205/3584* (2013.01); *A61M 2205/3592* (2013.01); *A61M 2205/50* (2013.01); *A61M 2205/52* (2013.01); *A61M 2205/581* (2013.01); *A61M 2205/582* (2013.01); *A61M 2205/583* (2013.01); *A61M 2205/6054* (2013.01)

(58) Field of Classification Search
  CPC ...... A61M 2205/50; A61M 2205/3592; A61M 2205/3584; A61M 2205/3569; A61M 2205/6054; A61M 2205/3324; A61M 2205/276; A61M 2205/27; A61M 5/31501; A61M 5/502; G16H 40/63; G06F 19/3468
  See application file for complete search history.

(56) References Cited

U.S. PATENT DOCUMENTS

| | | |
|---|---|---|
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 8,882,722 B2 * | 11/2014 | Bode ................ A61M 5/31525 604/207 |
| 10,058,655 B2 | 8/2018 | Kietzmann et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2008/0119796 A1 * | 5/2008 | Graf ..................... A61M 5/315 604/207 |
| 2009/0043253 A1 * | 2/2009 | Podaima ................ G06Q 10/10 604/67 |
| 2009/0275916 A1 | 11/2009 | Harms et al. |
| 2014/0330243 A1 | 11/2014 | Kietzmann et al. |

FOREIGN PATENT DOCUMENTS

| | | |
|---|---|---|
| EP | 0937471 A2 | 8/1999 |
| EP | 0937476 A2 | 8/1999 |
| EP | 1447105 A2 | 8/2004 |
| JP | 2001-17542 A | 1/2001 |
| JP | 2004-236734 A | 8/2004 |
| WO | 1999007425 A1 | 2/1999 |
| WO | 1999/38554 A1 | 8/1999 |
| WO | 2001/10484 A1 | 2/2001 |
| WO | 2007/041843 A1 | 4/2007 |
| WO | 2007/081947 A2 | 7/2007 |
| WO | 2009/132778 A1 | 11/2009 |
| WO | 2009/143255 A1 | 11/2009 |
| WO | 2010/128493 A2 | 11/2010 |
| WO | 2011/023631 A2 | 3/2011 |
| WO | 2011/042540 A1 | 4/2011 |
| WO | WO-2011042540 A1 * | 4/2011 ............... A61M 5/24 |

* cited by examiner

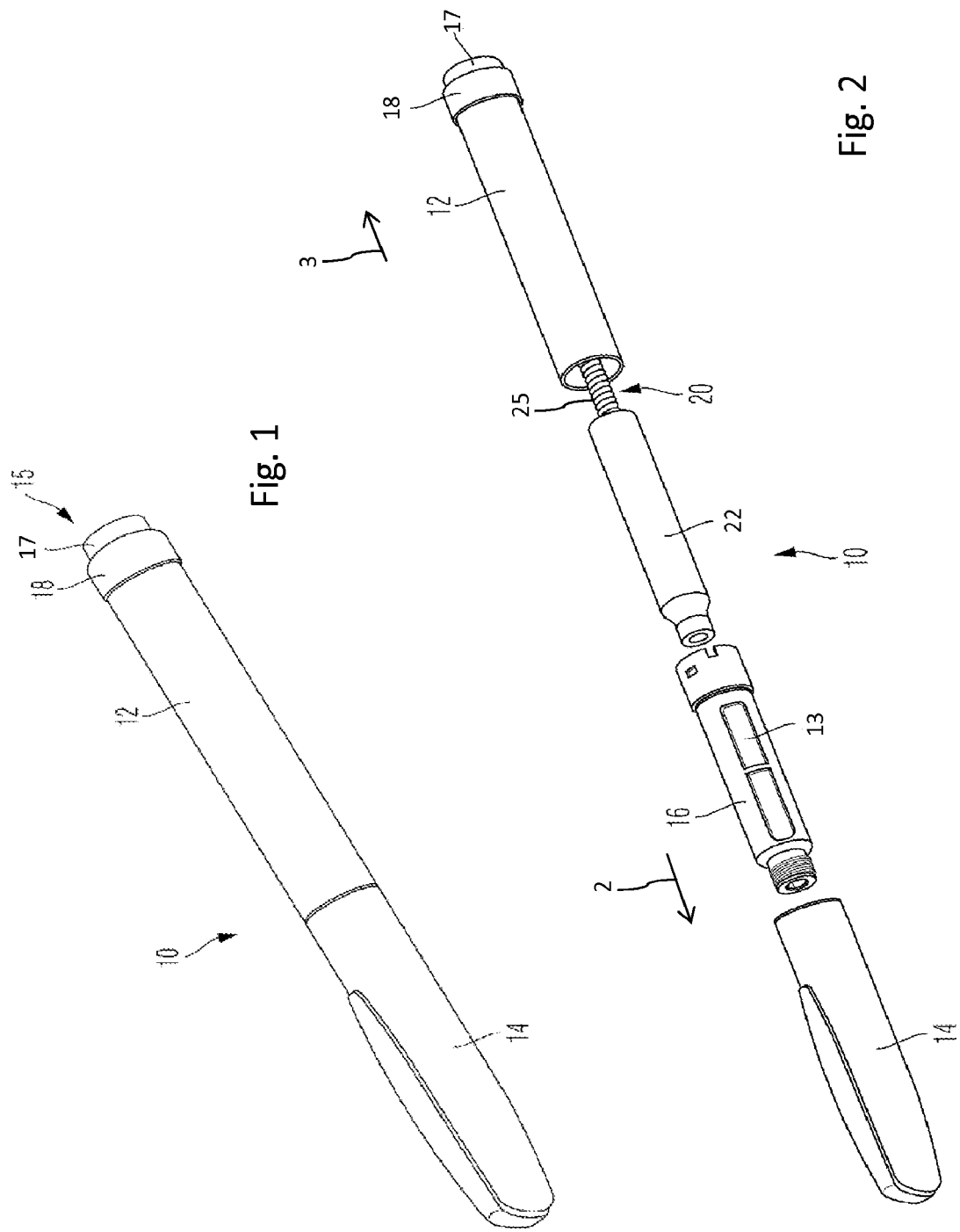

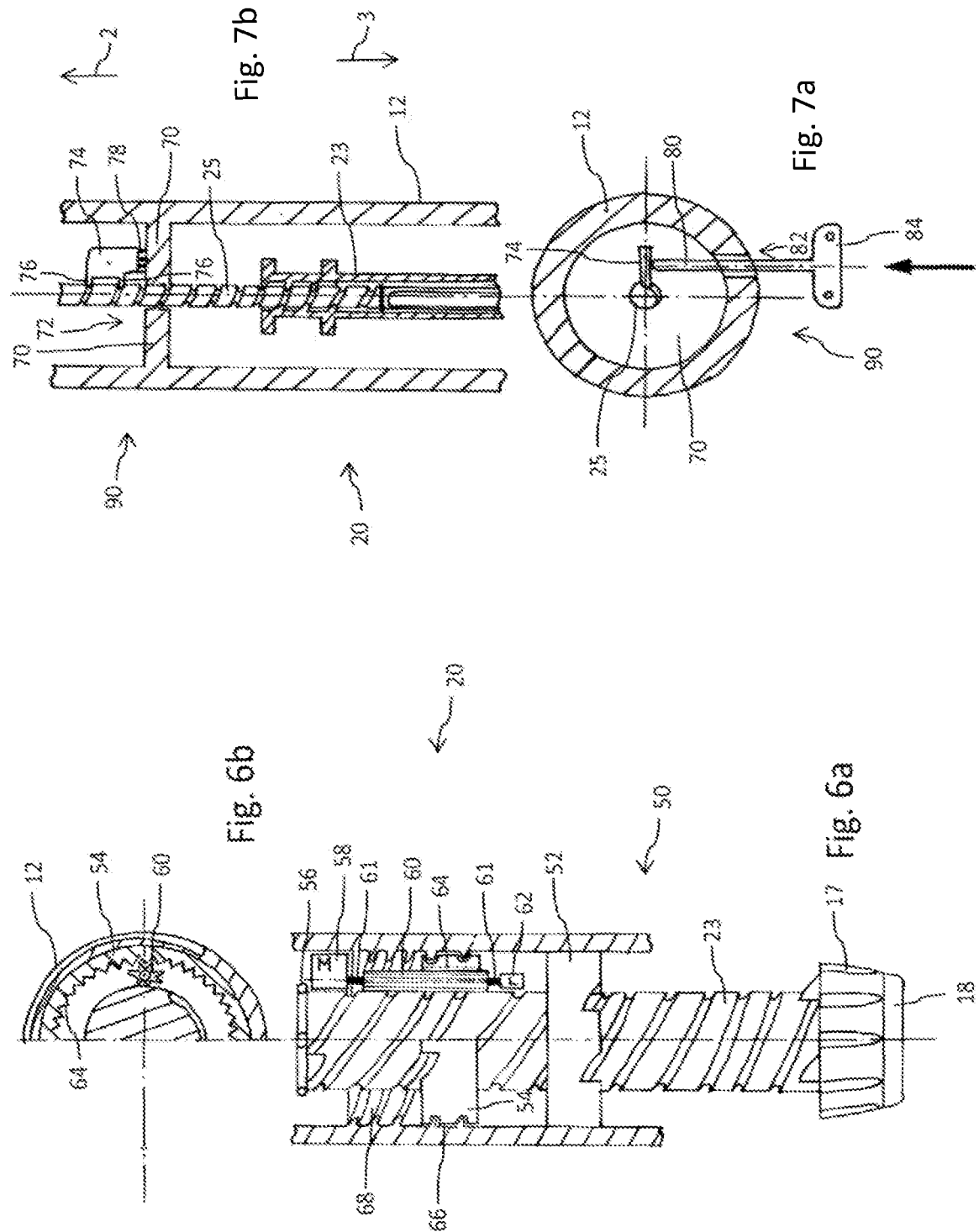

PEN-TYPE DRUG INJECTION DEVICE WITH CONTROLLER AND TIME LOCK-OUT MECHANISM FOR ITS DRIVE

CROSS REFERENCE TO RELATED APPLICATIONS

The present application is a continuation of U.S. patent application Ser. No. 14/359,383 filed May 20, 2014, which is a U.S. National Phase Application pursuant to 35 U.S.C. § 371 of International Application No. PCT/EP2012/072945 filed Nov. 19, 2012, which claims priority to European Patent Application No. 11190062.7 filed Nov. 22, 2011. The entire disclosure contents of these applications are herewith incorporated by reference into the present application.

FIELD OF INVENTION

The present invention relates to the field of drug delivery devices, in particular to the field of pen-type injectors adapted to set and to inject a dose of a medicament, preferably by way of injection in a self-medication environment.

BACKGROUND

Chronic diseases require administering of medicaments or drugs according to a predefined time schedule in order to keep the concentration level of a pharmaceutically active substance within given margins. Many medicaments require administration by way of injection. Therefore, patients administering the medicament in self-medication typically make use of syringes or syringe-like drug delivery devices. Such devices should be universally applicable and should be operable even by persons without formal medical training.

Moreover, such devices, like pen-type injectors, should provide accurate, precise and reliable setting of a dose and subsequent dispensing of the respective amount of the medicament. Typically, the medicament to be dispensed and injected is provided in a disposable or replaceable cartridge, such as a vial, an ampoule or a carpule comprising a piston slidably disposed therein to become operably engaged with a piston rod of a drive mechanism of the drug delivery device. The drive mechanism is adapted to apply thrust to the cartridge's piston in a distal direction in order to built-up a respective fluid pressure, which in turn induces dispensing of the liquid medicament via a dispensing or distal end of the cartridge being typically in fluid connection with a piercing element like an injection needle.

It is generally of importance, that the patient strictly follows a given prescription schedule. However with patients that already got used to the medicament for a long time or patients that suffer side effects of a chronic disease and which may be physically or mentally impaired, compliance of the prescription schedule is sometimes suboptimal. Since a large variety of existing, e.g. disposable drug delivery devices is implemented all-mechanically, it is also rather difficult for an attending physician to control, whether the patient strictly follows the given prescription schedule.

For instance document WO 2011/042540 A1 discloses a safety injection system having a multi-dose delivery module and a removable cap configured to cover a needle on a distal end of the dose delivery module. Said safety injection system further comprises a time lock operatively connected to the cap and the multi-dose delivery module. This way, an automatic lockout feature is provided so that certain users will be effectively prevented from accidental over medication. However, such an automated lockout feature always requires, that the patient or user of the device always returns the removable cap back onto the distal end of the dose delivery module after an injection procedure has been accomplished.

SUMMARY

It is therefore an object of the present invention to provide a drug delivery device and a drive mechanism featuring an improved safety mechanism in order to avoid over medication. It is a further object to provide intuitive and unambiguous support for a user in handling and/or to operating the drug delivery device. In particular, the invention serves to facilitate compliance with a given prescription schedule.

The invention relates to a drive mechanism for a drug delivery device having at least a piston rod to operably engage with a piston of a cartridge to displace the cartridge's piston in a distal direction during a dose dispensing action. Typically, the cartridge comprising a vial, carpule or ampoule is at least partially filled with the medicament to be dispensed by means of the drive mechanism. The drive mechanism is typically accommodated in a housing of a drug delivery device in such a way, that the piston rod, upon actuating of the drive mechanism, is displaced in distal direction, either by way of a sliding or a helical motion in order to exert a respective thrust to the piston. This way, a well-defined dose of the medicament can be expelled from the cartridge via a distal outlet, being typically coupled with a needle assembly, like a double-tipped injection needle allowing to deposit the dose into biological tissue of the patient.

The drive mechanism further comprises at least one actuation member mechanically coupled with the piston rod to induce a distally directed displacement of the piston rod when the actuation member is actuated, e.g. depressed by a user.

The drive mechanism further comprises a control, e.g. in form of a control unit or control module to ascertain at least one predefined condition of use of the drive mechanism and/or of the drug delivery device. The control is particularly adapted to monitor regular actuation of the device. The control is further adapted to analyze and/or to evaluate various parameters of the drug delivery device and to compare gathered parameters or data with a predefined prescription schedule.

This way, the control is adapted to determine, if a dose setting and dose dispensing is actually due and/or if a dose injection matches with the predefined condition of use of the device. Additionally, the drive mechanism comprises at least one interlock member coupled with the control to directly or indirectly mechanically obstruct displacement of the piston rod if the condition of use is not fulfilled.

According to the present application, the term "condition of use" comprises conditions, such as but not limited to
- that the device is used for medicament dispense, e.g. according to a predefined prescription schedule;
- that the drive mechanism is actuated;
- that a dose of a known size is dispensed
- that skin contact is established;
- that the user is authorized to use the device;
- that the medicament is usable and not spoiled or wasted;
- that the device requires priming, e.g. to remove air from the dispense channel by filling it with medicament;
- that a timer circuit enforces a minimum time period between subsequent dose dispensing actions.

In a first approach, the interlock member generally obstructs and impedes displacement of the piston rod right after a dose dispensing has been accomplished. This way, once a dose has been dispensed, the drug delivery device and in particular its drive mechanism is deactivated for at least a predefined period of time. After said time period has elapsed, the control serves to reset the drive mechanism, such that the condition of use is repeatedly fulfilled. The control is then adapted to transfer the at least one interlock member into a release configuration, in which the drive mechanism and its piston rod can be actuated for a subsequent dose setting and/or dose dispensing procedure.

The control and the at least one interlock member are designed as integral components of the drive mechanism and/or of the drug delivery device. This way, the control and the interlock member are enabled to deactivate and/or to obstruct operation of the drive mechanism. Even the risk of intentional improper handling or incorrect operation and use of the device and its drive mechanism can therefore be effectively decreased.

The drive mechanism can be implemented in an all-mechanical way. Hence, displacement of the piston rod leading to a dispensing of the medicament contained in the cartridge is derived from an actuation of the actuation member entirely conducted, exerted or provided by the user himself. The drive mechanism may comprise a storage module to store mechanical energy, e.g. by way of a spring energy accumulator. However, independent of the concrete embodiment of the drive mechanism, which may be implemented all-mechanically or a electro-mechanically, the at least one interlock member is adapted to mechanically obstruct operation of the drive mechanism and/or to impede displacement of the piston rod. Therefore, even with an electromechanically driven piston rod or drive mechanism of the drug delivery device, the invention may provide an on-device mechanical interlock to impede unintended and improper handling of the device.

According to a preferred embodiment, the interlock member is adapted to releasably engage with anyone of piston rod, drive member, actuation member or with any other component of the drive mechanism directly or indirectly mechanically engaged therewith. In principle, the interlock member may releasably engage with any component of the drive mechanism located in the torque- or force transferring system between actuation member, adapted to receive an actuation force, and piston rod, adapted to exert a dispensing force to the piston of the cartridge. Mutual engagement of the at least one interlock member and the at least one component of the drive mechanism can be implemented all-mechanically, e.g. in form of a latch- or clamping mechanism.

Moreover, also electromechanical or electromagnetic implementations of the interlock member are generally conceivable. The blocking or obstruction of the component of the drive mechanism to be provided by the interlock member can be implemented as a positive- or force-fitting interlock. Depending on the implementation of the piston rod, the interlock member may be either adapted to impede and/or to obstruct rotation and/or a sliding motion of the piston rod in distal and/or proximal direction.

According to a further embodiment, the control is adapted to monitor and/or to verify a user-driven actuation of the drive mechanism. Actuation of the drive mechanism may include a dose setting as well as a dose dispensing and may be accompanied by e.g. displacing the actuation member, which is typically located at a proximal end of the drug delivery device, in either direction, proximal or distal.

According to another preferred aspect, the control is adapted to verify whether actuation of the drive mechanism matches with at least one predefined condition of use. The control, typically implemented as an electronic control module is preferably adapted to store and to record subsequent actuation procedures or actuation instants of the drive mechanism. This way, the control may repeatedly acquire data being indicative of a time instant, at which actuation of the drive mechanism and/or dispensing of a dose of a known size has occurred. By comparing recorded data with a predefined prescription schedule to be configurably stored in the control, matching and compliance with predefined conditions of use can be determined.

According to another preferred aspect, the drive mechanism comprises numerous sensors or various modules and units in order to gather state information being indicative of the actual state of the drug delivery device. On the basis of such state information, compliance of the at least one condition of use can be determined. For this purpose, the drive mechanism may further comprise a pressure sensor mechanically coupled with the piston rod and/or with the piston of the cartridge. The drive mechanism may also comprise an authorization and/or communication module, a chemical analysis module, a skin touch sensor to register contact with the skin of a patient, a timer circuit, an electromechanical vibration module and/or at least one visual, audible and/or tactile indicator.

All aforementioned components may belong to the drive mechanism or may be integrated therein. They are particularly adapted to communicate with the control of the drive mechanism in order to determine whether the at least one predefined condition of use is met in order to release the interlock member and to allow operation and actuation of the drive mechanism. Alternatively, said components may be manufactured and/or positioned elsewhere in or on the drug delivery device and may be designed independent of the drive mechanism.

For instance, by way of the pressure sensor, mutual abutment between piston rod and piston of the cartridge can be determined. Hence, if the pressure exerted from the piston rod to the piston is or drops below a given threshold, priming of the drive mechanism and establishing of a tight mutual abutment of piston rod and piston of the cartridge may become necessary prior to dispensing of a dose from the cartridge.

Also, an authorization and/or communication module may sense, whether the person actually handling or actuating the device is authorized to do so. The person may be provided with a transponder and/or with an identification tag, e.g. on the basis of RFID-technology. The authorization and/or communication module is then adapted to communicate with the users' RFID tag or transponder in order to provide access to dose setting and/or dose dispensing actuation of the drug delivery device.

Further, by way of a chemical analysis module, usability of the medicament contained in the cartridge can be frequently monitored and controlled. For instance, the chemical analysis module may be adapted to investigate physical or chemical properties of the medicament, such like the pH-parameter, from which usability of the medicament can be derived.

Moreover, the drive mechanism may be equipped with a skin touch sensor, which may be disposed near a distal dispensing end of the drug delivery device. By way of a skin touch sensor, contact of the drug delivery device with biological tissue to receive the dose of the medicament can be precisely sensed. This way, the control may release a dose dispensing actuation only if a skin contact has been determined.

Additionally, the drive mechanism may be equipped with a timer circuit, which may even be embedded in the control module or assembled elsewhere in or on the drive mechanism and/or the drug delivery device. By way of the timer circuit, minimum time periods between subsequent dose dispensing actions can be enforced. Hence, the control may automatically deactivate and/or obstruct the drive mechanism for a predefined period of time after accomplishing of a previous dose dispensing. Since the control and interlock member are preferably designed as integral components of the drive mechanism, even intentional manipulation and overriding of this safety feature can be almost excluded.

By way of an electromechanical vibration module, the drive mechanism may interact with a user prior or during a dose setting and/or dose dispensing procedure. Since the self-medicating user typically holds the drug delivery device in at least one hand, vibration of the drive mechanism will be well perceived by the user even if visually or acoustically impaired.

Additionally or alternatively, the drive mechanism may be equipped with at least a visual, an audible and/or a tactile indicator. This way, the drive mechanism and the drug delivery device may either visually and/or acoustically and/or tactilely indicate to the user, whether a predefined condition of use is actually fulfilled and that the device is ready to be used.

The control may communicate with at least one, preferably with several of the above-mentioned components, sensors and modules in order to automatically determine, if a predefined condition of use is fulfilled.

According to a further preferred embodiment, the control is particularly configured to transfer the interlock member in a release mode only when the at least one condition of use is fulfilled. This way, the drive mechanism and/or at least its piston rod per default remains in an obstructed or interlocked configuration in order to effectively counteract unintended or unauthorized handling or application of the device.

Furthermore and according to another preferred embodiment, the interlock member is particularly adapted to releasably obstruct a user-initiated dose setting and/or a dose dispensing actuation if the condition of use is not fulfilled. In particular with mechanically implemented drive mechanisms, such like pen-type injectors, non-fulfillment of the condition of use may automatically lead to a complete obstruction and blocking of the drive mechanism. In this case, even a dose setting to be conducted prior to a dose dispensing, may be effectively prevented.

According to another aspect, the control is further capable to trigger a visual, an audible and/or a tactile indication to the user, that actuation of the device is due. This way, the drive mechanism may provide an integrated wakeup- or reminder function that serves to remind the patient to conduct a dose setting and/or dose dispensing procedure. Hence, the drive mechanism actively reminds the user of taking a dose of the medicament.

Moreover and according to another embodiment, the control is further capable to visually, audibly and/or tactilely instruct a user to correctly operate and to correctly handle the drive mechanism and/or the drug delivery device. Hence, the various steps of dose setting, eventual ventilating of a needle assembly, dose dispensing and waiting for a predefined dwell time prior to extract a needle assembly from biological tissue can be accompanied by the control. The various sensors and sensing modules may be adapted to provide respective information to the control in order to identify the various steps of operating and handling the drive mechanism and/or the drug delivery device. In response of detecting various handling steps, the control module may therefore provide respective visual, audible and/or tactile indications to the user, whether the device and/or the drive mechanism is actually correctly handled and operated or not.

In a further preferred aspect, the invention also relates to a drug delivery device, preferably to a pen-type injector being adapted to set and/or to dispense a dose of a medicament. The drug delivery device comprises a cartridge holder to receive a cartridge filled with the medicament to be dispensed. The device further comprises a housing or housing component to accommodate a drive mechanism. The housing is further to be operably connected with the cartridge holder. While the housing is preferably designed as a proximal housing component, the cartridge holder may serve as a distal housing component to be releasably or non-releasably interconnected with the proximal housing component.

Generally, it is also conceivable, that the drug delivery device comprises a single-pieced housing providing both a cartridge holder as well as a casing for the drive mechanism to interact with the cartridge. The drug delivery device further comprises a drive mechanism as described above in order to provide the above-mentioned functionality.

In a preferred embodiment, the drug delivery device also comprises a cartridge disposed in the cartridge holder and/or in the housing of the drug delivery device, wherein the cartridge is at least partially filled with the medicament to be dispensed by the drug delivery device.

In a further preferred embodiment, the housing of the drug delivery device and/or its cartridge holder comprise a visual, audible and/or tactile indicator to respectively indicate to the user whether a condition of use is actually fulfilled and whether dose setting and/or dose dispensing can be conducted or not.

In a further preferred aspect, the invention also refers to a method of operating a drug delivery device comprising a cartridge filled with a medicament and further comprising a drive mechanism as described above. The method of operating the drug delivery device comprises the steps of monitoring a dose setting and/or dose dispensing actuation of the drive mechanism by means of a control. Furthermore, at least one actual state parameter of the drug delivery device is determined and is further compared with at least one predefined condition of use of the drug delivery device.

If the actual state parameter does not match with the predefined condition of use, the drive mechanism will be mechanically obstructed by means of an interlock member of the drug delivery device adapted to releasably engage with an arbitrary, but force- or torque transmitting component of the drive mechanism. However, in case the determined state parameter matches with the at least one predefined condition of use, actuation of the drive mechanism, e.g. for dose setting and/or dose dispensing is released and the device can be used in a rather conventional way.

In a further aspect, the invention also refers to a method of operation of a drug delivery device comprising a cartridge filled with a medicament and further comprising a drive mechanism as described above. The method of operation comprises the steps of monitoring a dose setting and/or dose dispensing actuation of the drive mechanism by means of a control. Furthermore, at least one actual state parameter of the drug delivery device is determined and is further compared with at least one predefined condition of use of the drug delivery device.

If the actual state parameter does not match with the predefined condition of use, the drive mechanism will be mechanically obstructed by means of an interlock member of the drug delivery device adapted to releasably engage with an arbitrary, but force- or torque transmitting component of the drive mechanism. However, in case the determined state parameter matches with the at least one predefined condition of use, actuation of the drive mechanism, e.g. for dose setting and/or dose dispensing is released and the device can be used in a rather conventional way.

In a further preferred embodiment, the housing of the drug delivery device and/or its cartridge holder comprise a visual, audible and/or tactile indicator to respectively indicate to the user whether a condition of use is actually fulfilled and whether dose setting and/or dose dispensing can be conducted or not. The above mentioned method of operation of a drug delivery device further comprises the steps of indicating to the user whether a condition of use is actually fulfilled and indicating to the user whether dose setting and/or dose dispensing can be conducted or not.

In still another aspect, the invention also refers to a computer program comprising computer executable instructions being operable to determine at least one state parameter and/or to determine at least one predefined condition of use of the drug delivery device and/or of its drive mechanism. The instructions are further operable to compare the state parameter with the condition of use in order to execute the above-mentioned methods.

It is to be noted, that all features and embodiments as described herein are to be understood to equally apply to the drive mechanism, to the drug delivery device as well as to the method of operating the drug delivery device and its drive mechanism and to the computer program associated therewith. In particular, a mentioning of a component being configured or arranged to conduct a particular operation is to be understood to disclose a respective method or program step and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(0)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(0)14, Trp(O2)25, Asp28] Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the aforementioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings, in which:

FIG. 1 schematically illustrates a drug delivery device in form of a pen-type injector in a perspective view, FIG. 2 shows the drug delivery device according to FIG. 1 in an exploded perspective view, FIG. 6*a* is indicative of an electromechanical implementation of an interlock, FIG. 6*b* shows the interlock member of FIG. 6*a* in transverse cross section, FIG. 7*a* shows another embodiment of a mechanical interlock, and FIG. 7*b* depicts a cross section of the embodiment according to FIG. 7*a*.

DETAILED DESCRIPTION

Figure 3:
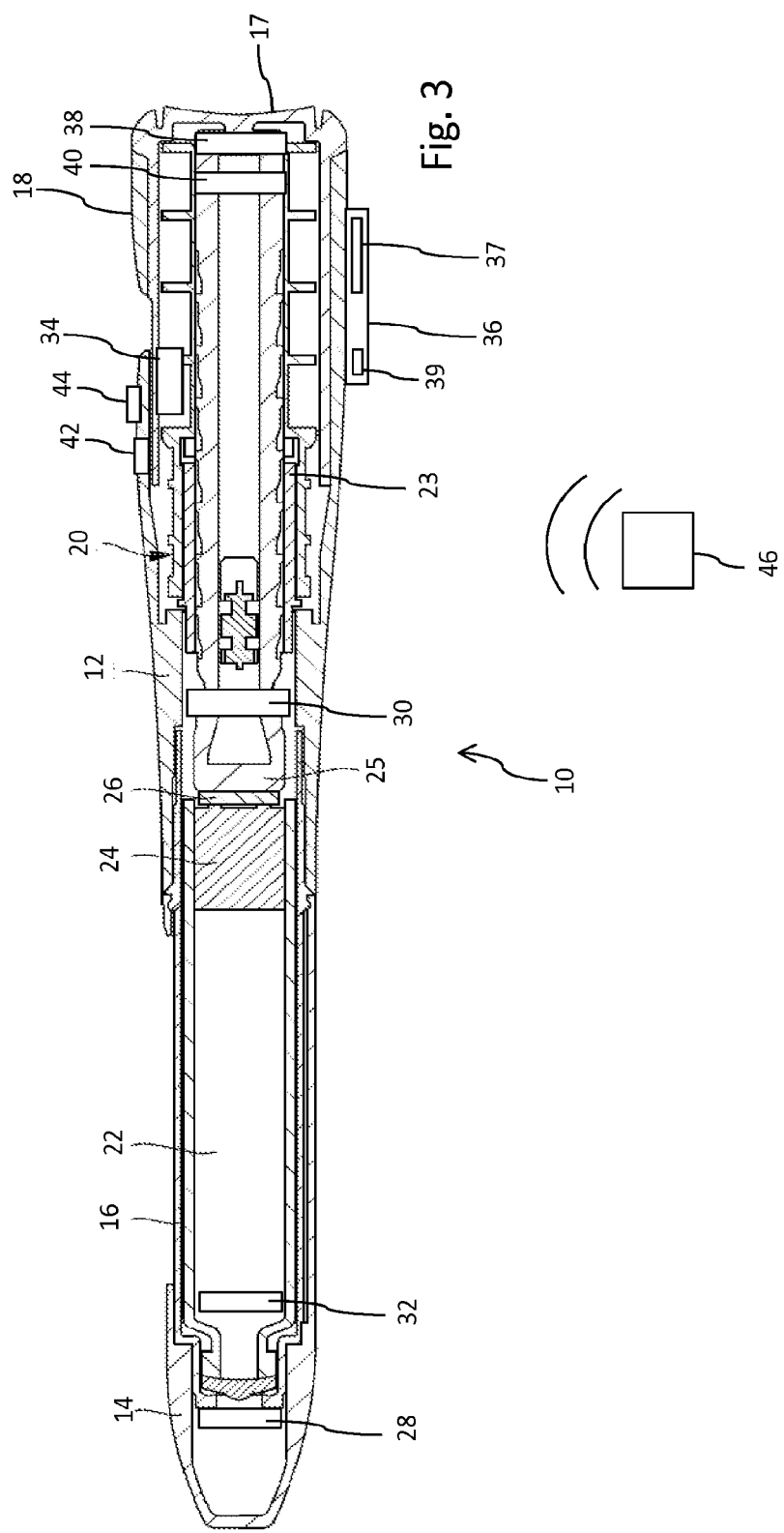
FIG. 3 shows a pen-type injector featuring various add-on modules and components to provide self-actuated obstruction and interlock of the device and/or of its drive mechanism.

The pen-type injector 10 as shown in FIGS. 1 and 2 comprises a proximal body or housing component 12 and a distally located cartridge holder 16 that serves to accommodate a cartridge 22 being at least partially filled with a medicament to be injected. The proximal housing component 12 serves to accommodate a drive mechanism 20, which is not explicitly illustrated in FIGS. 1 and 2. The drive mechanism 20 at least comprises a piston rod 25 to operably engage with a piston of the cartridge 22.

The drive mechanism 20 further comprises a dose dial 18 as well as an injection button 17, by way of which a dose of the medicament can be set and dispensed. The dose dial 18 and the injection button 17 are located at a proximal end 15 of the drug delivery device 10.

The drive mechanism 20 is preferably implemented all-mechanically. For instance when rotating the dose dial 18 clockwise or counter-clockwise relative to the housing 12, the dose button 17 together with the dose dial 18 and an optional dose dial sleeve 23 may extend or displace in proximal direction 3 relative to the housing 12. As soon as a predefined dose is set, depressing the dose button 17 in distal direction 2 may induce a rotative and/or sliding motion of the piston rod 25, thereby displacing the piston of the cartridge 22 in distal direction 2. This way, the liquid medicament contained in the cartridge 22 can be expelled via a needle assembly to be releasably mounted on a threaded socket of the cartridge holder 16. When not in use, the device 10, in particular its cartridge holder 16 and cartridge 22 are to be covered with a protective cap 14. The cartridge holder also comprises an inspection window 13 by way of which the filling level of the cartridge 22 disposed therein can be visually inspected.

The overall design of the drug delivery device 10 as depicted in FIG. 3 may slightly deviate from the drug delivery device 10 as shown in FIGS. 1, 2 and FIGS. 5 to 7. However, since the various illustrated devices 10 and drive mechanisms 20 provide substantially comparable functionalities, the same or similar device components are denoted with identical reference numerals in the illustrated Figures.

As indicated in FIG. 3, the drive mechanism 20 of the drug delivery device 10 comprises at least one interlock member 30 being coupled with a control or control unit 36 in order to mechanically obstruct displacement of the piston rod 25 if a condition of use of the drive mechanism is not fulfilled. The interlock member 30 may comprise a latch or clutch-mechanism and may mechanically engage with the piston rod 25 in order to obstruct a longitudinal displacement or rotation thereof relative to the housing 12. The interlock member 30 may also releasably engage with any other component of the drive mechanism. Hence, it is conceivable, that the interlock member 30 engages with either the dose dial 18, with the injection button 17 and/or with the dose dial sleeve 23.

The control 36 further comprises or provides a time lock 37 adapted to frequently interlock or to frequently obstruct the piston rod 25 or the entire drive mechanism 20 for a predefined period of time. In this way, the risk, that a certain medicament is injected or dispensed too often can be minimized.

The control 36 and/or the interlock member 30 may be implemented all mechanically. The timer functionality of the control 36 may for instance also be integrated into the interlock member 30. A mechanical time lock may for instance be implemented in form of a clockwork which automatically activates with accomplishment of a previous dose dispensing action. Then, the clockwork or interlock member 30 may automatically and mechanically obstruct and impede repeated and immediate actuation of the drive mechanism 20 for a predefined period of time.

Alternatively, the control 36 can be implemented as an electronic device, wherein a time-lock functionality is implemented by way of an electronic circuit 37 serving as a timer module. The control 36 may be further equipped with a storage 39 in order to monitor and to log frequent and subsequent dose setting and dispensing procedures. This way, the module 36 may gather information about the total amount of medicament dispensed during a given period of time.

The drive mechanism 20 and/or the drug delivery device 10 also comprise a kind of power supply 38. In case of an electronic implementation of the control the power supply 38 comprises a battery, which may be rechargeable. With an all-mechanical implementation of the control 36, e.g. comprising a clockwork-like time-lock, the power supply 38 may comprise a spring energy accumulator, adapted to store mechanical energy in response of a user actuating the device. Moreover, the power supply 38 may comprise at least one converter, like a piezo-element, adapted to transfer mechanical power provided by a user into electric energy.

The control 36 may further monitor the status of the battery. Hence, when the power provided by the battery 38 drops below a given threshold, the control 36 may permanently interlock the drive mechanism 20 and may indicate to the user, that a change of the battery 38 is due soon.

Also, when inserting a new and filled cartridge 22 into the device 10, an injection counter of the control 36 may be manually or automatically reset. This way, the control 36 is able to provide information regarding the filling level of the cartridge. The control 36 is further coupled with a visual indicator 42 and/or with an acoustic indicator 44. The visual indicator 42 may be implemented as a light emitting diode (LED) or may comprise several LED that may feature different colours, like red and/or green.

The audible indicator 44 may comprise a speaker or some other acoustical indication means, like a buzzer, being at least capable to generate an acoustic alert. Additionally, the control 36 itself may feature a display in order to provide detailed information to a user, e.g. regarding the general device status and/or regarding conditions of use. The drive mechanism 20 may be further equipped with a vibration unit 40 that may feature a piezodrive allowing to set the entire device in a vibrational movement. This way, device-specific or prescription-schedule-specific information can be communicated to a user or patient in many different ways.

Interaction between control 36, interlock member 30 and indicating means 40, 42, 44 on the one hand allows to obstruct the drive mechanism 20 and to indicate to a user, that the device 10 is blocked or deactivated for a predefined period of time. On the other hand, the various indicators 36, 40, 42, 44 may also be used to indicate and/or to remind a user, that the next application of a dose is due.

The control 36 may also monitor the size of a dose set by a user and may compare the set dose size to be subsequently dispensed with the amount of the medicament still available in the cartridge 22. In the event, that the set dose exceeds the amount of medicament provided in the cartridge 22, the drive mechanism may either obstruct and indicate to a user that replacement of the cartridge 22 is due. Alternatively, the drive mechanism 20 and/or its control 36 may indicate the size of insufficient rest volume contained in the cartridge 22 and may still allow to dispense the residual amount of the medicament provided in the cartridge 22.

After completion such an insufficient dispensing, the control 36 may generate respective alerts or indications, that the cartridge 22 is to be immediately replaced and that a further amount of the medicament is still to be injected.

Moreover, by permanently monitoring the filling level of the cartridge 22, the control 36 may also be adapted to indicate to a user, that replacement of a cartridge 22 is due soon.

Additionally, the control 36 may also monitor, whether the expiry day of the medicament provided in the cartridge 22 has already been reached. Hence, the control 36 may store and/or record initial use of the medicament and may calculate a particular day after which the medicament should no longer be dispensed. If the expiry day of the medicament has been reached, the control 36 is adapted to automatically obstruct the drive mechanism 20. Then, the patient is enforced to replace the cartridge 22 by a new one. This way, a danger of misuse of a medicament can be effectively reduced.

Additionally, the control 36 may be programmable, e.g. by means of a programming device by way of which an attending physician or other authorized medical personal stores a predefined prescription schedule in the memory 39 of the control 36. Depending on the programming, the control 36 may either impede and/or encourage setting and/or dispensing of subsequent doses according to the given schedule. By storing respective injection and dosage information, the attending physician may also read out the storage 39 of the control 36 in order to monitor actual use of the device and to check, whether compliance with the given prescription schedule is attained.

Additionally, the drive mechanism 20 may comprise a communication and/or authorization module 34. The communication module 34 may be implemented wireless and may provide communication, preferably according to standard communication protocols, like RFID, Bluetooth or the like. By way of the communication and/or authorization module 34, the drive mechanism 20 and/or the drug delivery device 10 may communicate with an external transponder 46. This way, a kind of wireless keylock can be implemented in such a way, that release of the drive mechanism 20 only occurs in response to a detection of the transponder 46 being positioned within a predefined range in the vicinity of the drug delivery device 10.

Additionally, the transponder 46 may serve as a pager and may induce some kind of audible or visual alert by way of the wireless communication with the communication module 34. In case the patient is unaware of the actual location of the drug delivery device, he may induce a paging alert by way of the transponder 46, which is e.g. permanently kept by the user. In response to receive a paging signal from the transponder 46, the control 36 may induce an audible, visual or even vibrational alert by way of LED 42, speaker 44 and/or vibration unit 40. Also the transponder 46 may regularly send a paging signal to the drug delivery device in order to verify that the device 10 remains in close proximity to the user or patient. In situations the user e.g. intends to leave his home environment, the transponder 46 will check, if the user is keeping the drug delivery device 10 with him.

It is even conceivable, that the transponder 46 is used to indicate to the user, that the next dose setting and dispensing procedure is due. Then, the device 10 may transmit respective alert signal to the transponder 46, which in response to the received signal may generate a respective audible, vibrational or visual alert.

The drive mechanism 40 may be further coupled and connected with a skin touch sensor 28 allowing to determine, whether the device 10 is in contact with biological tissue intended and/or adapted to receive the dose of the medicament. As long as the skin touch sensor 28 transmits a respective signal to the control 36, that the skin of the patient has not yet been touched or pierced, the control 36 may hinder the drive mechanism 20 from dispensing of a dose already set.

Additionally, the drive mechanism 20 and/or the control 36 may communicate with a chemical analysis module 32, which is adapted to determine usability of the medicament contained in the cartridge 22. Hence, the chemical analysis module 32 may for instance be adapted to determine a pH-parameter of the medicament, which may be indicative, whether the pharmaceutical substance is still usable. In case an inappropriate pH-parameter is detected thereby indicating that the expire date has been exceeded, the chemical analysis module 32 generates a respective signal to the control 36, which then obstructs the drive mechanism 20, e.g. by way of the interlock member 30.

Furthermore, the drive mechanism 20 may be equipped with a pressure sensor 26 arranged between piston rod 25 and piston 24 of the cartridge 22. This way, mutual abutment of piston 24 and piston rod 25 can be precisely determined and/or monitored. Also, further procedural steps during or prior dose setting and dispensing can be precisely monitored and various functions, such like dose setting or dose dispensing can be blocked or obstructed if the user does not follow a predefined application procedure. The various sensors and detection modules allow to monitor, whether for instance a mandatory safety shot has been executed prior to an injection into biological tissue. Moreover, also a predefined dwell time, an injection needle should remain in the biological tissue after completion of dose dispensing can be at least indicated to the user.

Generally, by way of the various modules, sensors and by way of the control 36 a general access control as well as an effective child lock can be provided. Also, the drive mechanism 20 may enforce complete emptying of a cartridge 22 prior to cartridge replacement. The drive mechanism 20 may be individually programmed and configured to enforce and to provide user specific dispensing of subsequent doses of a medicament. Improper handling, operation or use of the device 10 may be at least recorded and may be displayed to the attending physician later on.

Figure 4:
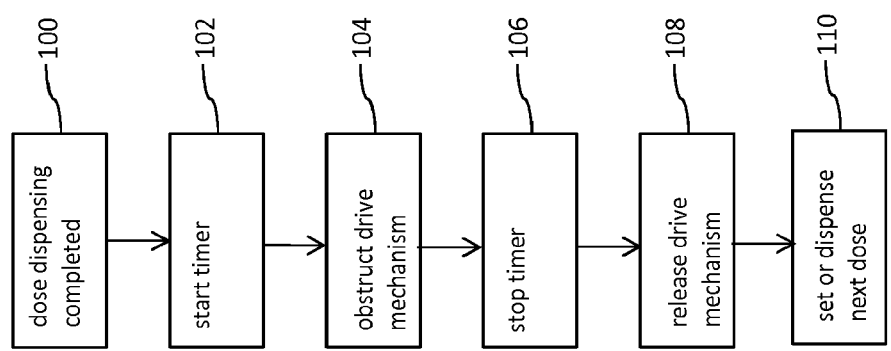
FIG. 4 is illustrative of a flowchart of a method to operate the drug delivery device.

FIG. 4 is further illustrative of the various steps of handling and/or operating the device. Starting from a previous dose setting and dose dispensing procedure accomplished in step 100, a timer 37 will be for instance automatically started in step 102 by the control 36, either mechanically and/or electronically. The activated timer deactivates use of the device and the interlock member 30 is therefore activated impeding immediate setting and/or dispensing of the next dose in step 104.

When the predefined time interval has passed in step 106, the control 36 will deactivate the interlock member 30, thereby reactivating the dose setting and/or dose dispensing functionality in step 108. In a subsequent step 110 a subsequent dose can be set and/or dispensed.

The illustrated method is not limited to the timer as an example of a condition of use but universally applies to various different condition of use parameters, like battery life time, lifetime of the medicament, filling level of the cartridge, dosing history and/or prescription schedule.

Figure 5:
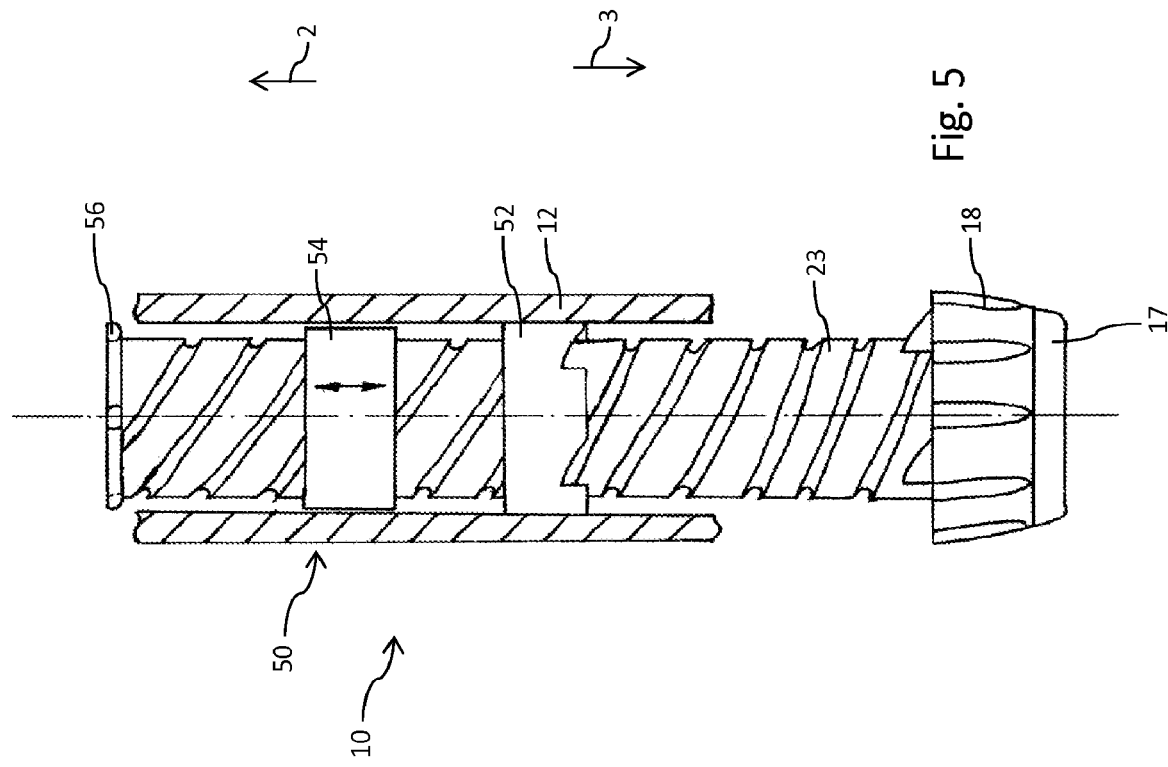
FIG. 5 shows a mechanical implementation of an interlock member.

FIG. 5 is further illustrative of a non-limiting example to implement a mechanical interlock member 50. There, the drive member 23 of the drive mechanism 20 is threadedly supported in a correspondingly threaded insert 52. By setting the drive member 23 in a screwing motion, e.g. by way of the dose dial 18 interconnected therewith, the drive member 23 will become subject to an axial displacement, either in proximal direction 3 or distal direction 2.

Additionally, the drive member 23 is engaged with a locking sleeve 54, preferably in a sliding or frictional way. The locking sleeve 54 is preferably engaged with the inside facing side wall of the housing 12. Since the locking sleeve 54 is separated from the insert 52 in distal direction 2 it can serve as an axial stopper for the drive member 23. The drive member 23 further has a distal stop element 56 extending radially outwardly from the drive member 23 at a distal end thereof. When the drive member 23 is for instance displaced in proximal direction 3, the stop element 56 is correspondingly displaced in proximal direction until its outer rim buts with the locking sleeve 54 being engaged with and fixed to the housing 12.

Preferably, the locking sleeve 54 is displaceably mounted in the housing 12. When positioned near the distally located stopper 56 of the drive member 23, the locking sleeve provides a kind of mechanical interlock, effectively impeding and preventing any proximally directed displacement of the drive member 23, e.g. for setting a dose. Positioning of the stopper 56 in a distal stop position therefore effectively obstructs activation and operation of the drive mechanism 20.

Moreover, when positioning the locking sleeve 54 at a predetermined axial position, a dose size limit can be provided. Hence, proximally directed displacement of the drive member 23 can be effectively delimited. A physician or other authorized medical staff may arrange the locking sleeve 54 in a predetermined axial position.

As further illustrated in the embodiment as shown in FIGS. 6a and 6b, the locking sleeve 54 is threadedly engaged with an inside facing side wall section of the housing 12. The locking sleeve 52 comprises an outer thread 66 which corresponds with an inner thread 68 of the housing 12. Here, the pitch of the mutually corresponding threads 66, 68 is of self-locking type. Hence an axially directed force between locking sleeve 54 and housing 12 does not induce a rotation of the locking sleeve 54 relative to the housing 12.

Moreover, axial displacement of the locking sleeve 54 can be attained by way of an electrically operated drive 58. The drive 58, typically to be controlled by the control 36 is mechanically coupled with a drive shaft 61 arranged in a bearing 62 located proximally from the drive 58. The drive shaft 61 comprises an axially elongated gear 60, which is engaged with a corresponding inner thread 64 of the locking sleeve 54. By rotating the shaft 61 and its gear 60, the locking sleeve 54 is set in rotational movement with respect to the housing 12, which comes along with an axial displacement of the locking sleeve 54 relative to the housing 12. This way, the axial distance between the locking sleeve 54 and the stopper 56 can be modified.

In the embodiment as illustrated in FIGS. 6a and 6b, the drive 58 is located distally from the locking sleeve 54. In an alternative embodiment, not illustrated here, it is also conceivable that drive 58, shaft 61, axially elongated gear 60 and bearing 62 are arranged on a proximal side of the locking sleeve 54. This way, a direct mutual abutment configuration between locking sleeve 54 and stopper 56 can be attained, e.g. in order to obstruct and/or to block operation of the drive mechanism 20 on demand.

FIGS. 7a and 7b further illustrate another embodiment of an interlock member 90. Here, an interlock element 74 is arranged near a distal end of the housing 12 to engage with the piston rod 25 of the drive mechanism 20. The piston rod 25 is threadedly engaged with a correspondingly threaded distal insert 70 portion of the housing 12. Therefore, the piston rod 25 is axially displaceable with respect to the housing 12 in a screw like motion. A respective screwing and rotating motion can be induced e.g. by exerting thrust to the dose button 18 in distal, hence dispensing direction. A distal displacement of the dose button 18 incurs a corresponding distally directed displacement of the drive member 23 threadedly engaged with a proximal portion of the piston rod 25. Since the threaded engagement of drive member 23 and piston rod 25 is of non-self-locking type, the piston rod 25 will become subject to a rotational movement in response of a distally directed displacement of the drive member 23.

The interlock member 74 is arranged on the threaded insert 70 near a central and threaded through opening 72 thereof. The interlock member 74 comprises radially inwardly extending interlock- and finger-like protrusions that engage and match with the outer thread of the piston rod 25. In the interlock configuration as shown for instance in FIG. 7a, any axial displacement of the piston rod 25 relative to the housing 12 is effectively impeded and obstructed.

The interlock member 74 is for instance pivot mounted to the insert portion 70 by way of a pivot axis 78 extending substantially parallel to the extent of the piston rod 25. By means of a radially extending pin 80 the interlock member 74 can be alternately disposed and positioned between the illustrated interlock configuration and a pivoted release configuration. As shown in FIG. 7b the pin 80 may either comprise a handle 84 or gripping end radially extending through a lateral through opening 82 of the housing 12.

By means of the pin 80 and the handle 84 the interlock member 90 can be reversibly or irreversibly transferred between an interlock and a release configuration, either manually or by way of a respective drive, which is not explicitly illustrated here.

Moreover and according to another alternative, it is also conceivable that the interlock element 74 is irreversibly detachable with regard to the insert 70. Instead of a pivoting arrangement, the interlock element 74 can be connected and attached to the insert 70 by way of a predetermined breaking portion. Then, the interlock element 74 may be irreversibly displaced in a release configuration e.g. by means of the pin 80.

What is claimed is:

1. A drive mechanism for a drug delivery device, the drug delivery device comprising a housing and a cartridge holder, wherein the cartridge holder is configured to accommodate a cartridge and is fixable to the housing, the drive mechanism comprising:
    a piston rod that is threadedly engaged with the housing of the drug delivery device and that is configured to operably engage with a piston of the cartridge to displace the piston in a distal direction during a dose dispensing action;
    at least one actuation member mechanically coupled with the piston rod and configured to induce a rotation of the piston rod relative to the housing thereby causing a distally directed displacement of the piston rod when the at least one actuation member is actuated by a user;
    an electronic control configured to ascertain at least one predefined condition of use;
    at least one interlock member coupled with and controlled by the electronic control, the at least one interlock member comprising one of a latch mechanism or a clamping mechanism configured to mechanically obstruct a rotation of the piston rod when the at least one condition of use is not fulfilled, and configured to release and allow a rotation of the piston rod when the at least one condition of use is fulfilled; and
    a communication and authorization module configured for wireless communication with an external transponder and configured to provide a wireless keylock for permitting a rotation of the piston rod only in response to a detection of the transponder being positioned within a predefined range of the communication and authorization module.

2. The drive mechanism according to claim 1, wherein the at least one interlock member is adapted to releasably engage with the piston rod, a drive member, the at least one actuation member, a dose dial, an injection button, a dose dial sleeve, or any combination of the aforementioned.

3. The drive mechanism according to claim 1, wherein the electronic control is adapted to monitor a user-driven actuation of the drive mechanism, to verify a user-driven actuation of the drive mechanism, or both.

4. The drive mechanism according to claim 1, wherein the electronic control is adapted to determine if the at least one predefined condition of use is fulfilled.

5. The drive mechanism according to claim 1, wherein the electronic control is configured to communicate with one or more of:
    a pressure sensor coupled with the piston rod;
    the communication and authorization module;
    a chemical analysis module configured to determine usability of a medicament contained in the cartridge;
    a skin touch sensor configured to register contact with the skin of a patient;
    a timer circuit;
    an electromechanical vibration module; and
    a visual, audible and/or tactile indicator.

6. The drive mechanism according to claim 1, wherein the electronic control is further configured to transfer the interlock member into a release mode only when the at least one condition of use is fulfilled.

7. The drive mechanism according to claim 1, wherein the at least one interlock member is adapted to releasably obstruct a user-initiated dose setting, a dose dispensing actuation, or both if the at least one condition of use is not fulfilled.

8. The drive mechanism according to claim 1, wherein the electronic control is further configured to trigger a visual indication, an audible indication, and/or a tactile indication that actuation of the device is due.

9. The drive mechanism according to claim 1, wherein the electronic control is further configured to visually, audibly and/or tactilely instruct a user to correctly operate the drive mechanism.

10. A drug delivery device to set and to dispense a dose of a medicament, the drug delivery device comprising:
    a cartridge holder to receive a cartridge filled with a medicament;
    a drive mechanism as recited in claim 1; and
    a housing to accommodate the drive mechanism, the housing being operably connected to the cartridge holder and fixed to the cartridge holder.

11. The drug delivery device according to claim 10, further comprising a cartridge at least partially filled by the medicament disposed in the cartridge holder.

12. The drug delivery device according to claim 10, wherein the housing, the cartridge holder, or both comprise a visual, audible and/or tactile indicator to indicate to the user whether a condition of use is actually fulfilled.

13. A drug delivery system comprising:
    an external transponder; and
    a drug delivery device to set and to dispense a dose of a medicament, the drug delivery device comprising:
        a cartridge holder to receive a cartridge filled with a medicament;

a housing to accommodate a drive mechanism, the housing being operably connected with the cartridge holder and fixed to the cartridge holder;

the drive mechanism comprising a piston rod threadedly engaged with the housing and configured to displace the piston in a distal direction during a dose dispensing action through a rotation of the piston rod relative to the housing;

an electronic control to ascertain at least one predefined condition of use;

at least one interlock member coupled with and controlled by the electronic control, the at least one interlock member comprising one of a latch mechanism or a clamping mechanism configured to mechanically obstruct a rotation of the piston rod when the at least one condition of use is not fulfilled, and configured to release and allow a rotation of the piston rod when the at least one condition of use is fulfilled; and a communication and authorization module configured for wireless communication with the external transponder and configured to provide a wireless keylock for permitting a rotation of the piston rod only in response to a detection of the transponder being positioned within a predefined range of the communication and authorization module.

14. The drug delivery system of claim 13, wherein the external transponder is configured to induce an audible or visual alert when receiving a wireless signal from the communication and authorization module.

15. The drug delivery system of claim 13, wherein the electronic control is configured to induce an audible, visual or vibrational alert in response to a wireless paging signal from the external transponder.

16. The drug delivery system of claim 15, wherein the external transponder is configured to automatically and regularly transmit a wireless paging signal.

17. A method of operating a drug delivery device comprising a housing, a cartridge filled with a medicament, and a drive mechanism including a piston rod threadedly engaged with the housing of the drug delivery device, wherein the drive mechanism is configured to displace the piston in a distal direction during a dose dispensing action through a rotation of the piston rod relative to the housing, the method comprising:

monitoring a dose setting and/or dose dispensing actuation of the drive mechanism by means of an electronic control;

determining at least one actual state parameter of the drug delivery device and comparing the at least one actual state parameter with at least one predefined condition of use of the drug delivery device;

wirelessly communicating with an external transponder through a communication and authorization module of the drive mechanism;

mechanically obstructing or releasing actuation of the drive mechanism in response to the comparison of the at least one actual state parameter and the at least one predefined condition; and permitting a rotation of the piston rod by one of a latch mechanism or a clamping mechanism only in response to a detection of the external transponder positioned within a predefined range of the communication and authorization module.

18. One or more non-transitory machine-readable media storing instructions executable by one or more processing devices of a drug delivery device, the drug delivery device including a housing, a medicament, and a drive mechanism including a piston rod threadedly engaged with the housing, wherein the drive mechanism is configured to displace the piston in a distal direction during a dose dispensing action through a rotation of the piston rod relative to the housing, wherein execution of the instructions causes the one or more processing devices to implement a method, the method comprising:

monitoring a dose setting and/or a dose dispensing actuation of the drive mechanism of the drug delivery device;

determining at least one actual state parameter of the drug delivery device based on the monitoring;

comparing the determined at least one actual state parameter with at least one predefined condition of use of the drug delivery device; and based on the comparison indicating that the at least one predefined condition of use of the drug delivery device is satisfied, sending a signal to mechanically release actuation of the drive mechanism for dispensing the medicament; or based on the comparison indicating that the at least one predefined condition of use of the drug delivery device is not satisfied, sending a signal to mechanically block actuation of the drive mechanism for dispensing the medicament by mechanically obstructing rotation of the piston rod through one of a latch mechanism or a clamping mechanism.

19. The one or more non-transitory machine-readable media of claim 18, wherein the method further comprises:

receiving a signal from a communication and authorization module of the drug delivery device indicating whether an external transponder is detected within a predefined range of the communication and authorization module; and sending a signal to permit rotation of the piston rod to dispense the medicament in response to a signal indicating that the external transponder is detected within the predetermined range; or sending a signal to prevent rotation of the piston rod to prevent the medicament from being dispensed in response to a signal indicating that the external transponder is not detected within the predetermined range.

* * * * *